United States Patent [19]
Giordani et al.

[11] Patent Number: 6,048,896

[45] Date of Patent: Apr. 11, 2000

[54] 4-PHENYL-4-OXO-2-BUTENOIC ACID DERIVATIVES WITH KYNURENINE-3-HYDROXYLASE INHIBITING ACTIVITY

[75] Inventors: Antonio Giordani; Paolo Pevarello, both of Pavia; Carmela Speciale, Nerviano; Mario Varasi, Milan, all of Italy

[73] Assignee: Pharmacia & Upjohn S.p.A., Milan, Italy

[21] Appl. No.: 09/068,103

[22] PCT Filed: Oct. 16, 1996

[86] PCT No.: PCT/EP96/04517

§ 371 Date: May 4, 1998

§ 102(e) Date: May 4, 1998

[87] PCT Pub. No.: WO97/17316

PCT Pub. Date: May 15, 1997

[30] Foreign Application Priority Data

Nov. 3, 1995 [GB] United Kingdom .................. 9522617

[51] Int. Cl.⁷ ............................ A01N 37/10; C07C 69/76
[52] U.S. Cl. ...................... 514/545; 514/538; 514/570; 514/618; 514/619; 560/51; 560/11; 560/12; 562/429; 562/430; 562/434; 562/459

[58] Field of Search ...................... 514/545, 538, 514/570, 618, 619; 560/51, 11, 12; 562/429, 430, 434, 459

[56] References Cited

U.S. PATENT DOCUMENTS

5,519,055  5/1996  Schwarcz et al. .
5,708,030  1/1998  Schwarcz et al. .

*Primary Examiner*—Paul J. Killos
*Attorney, Agent, or Firm*—Oblon, Spivak, McClelland, Maier & Neustadt, P.C.

[57] ABSTRACT

4-Phenyl-4-oxo-butenoic acid derivatives for use in the treatment of the human or animal body by therapy; particularly as kynurenine-3-hydroxylase inhibitors, in the prevention and/or treatment of a neurodegenerative disease wherein the inhibition of such an enzyme is needed. The present invention further comprises a selected class of the above mentioned 4-phenyl-4-oxo-butenoic acid derivatives, their pharmaceutically acceptable salts, a process for their preparation and pharmaceutical compositions containing them.

7 Claims, 1 Drawing Sheet

FIG. 1

4-PHENYL-4-OXO-2-BUTENOIC ACID DERIVATIVES WITH KYNURENINE-3-HYDROXYLASE INHIBITING ACTIVITY

The present invention refers to the use in the prevention and/or treatment of neurodegenerative diseases, such as, for example, Huntington's chorea, Alzheimer's disease, dementia caused by acquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammations of the brain, of 4-phenyl-4-oxo-2-butenoic acid derivatives which act as inhibitors of kynurenine 3-hydroxylase (KYN-3-OHase), an enzyme involved in the metabolism of kynurenine. This invention further comprises novel compounds, either as Z or E geometric isomers, which represent a selected class of the above mentioned 4-phenyl-4-oxo-2-butenoic acid derivatives, their pharmaceutically acceptable salts, a process for their preparation, and pharmaceutical compositions containing them.

Figure 1:
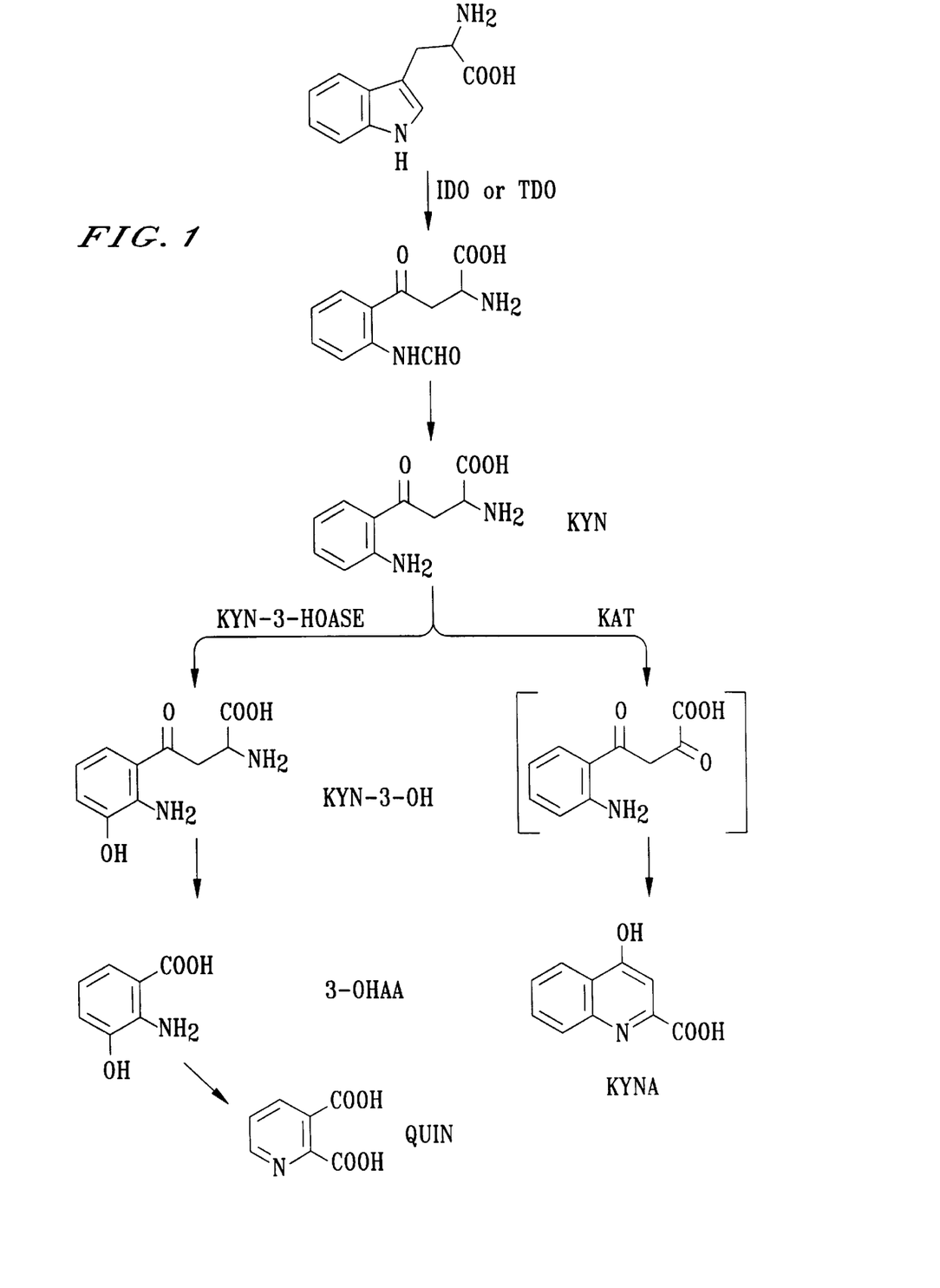

It is well known in the art that through the kynurenine (KYN) pathway, tryptophan metabolism gives rise to the formation of quinolinic acid (QUIN) on the one side and kynurenic acid (KYNA) on the other, as shown in FIG. 1.

In the last decade, several lines of evidence have demonstrated that two intermediates of the kynurenine metabolism, (QUIN) and (KYNA), when injected in the CNS, act as a neurotoxin and as a neuroprotective agent, respectively. Consequently, the demonstration that these two metabolites of the kynurenine pathway (unable to cross the blood brain barrier), are normal constituents of the mammalian brain, reveals the existence of this pathway within the CNS and proposes the involvement of QUIN and KYNA in brain physiology and pathology (Stone T. W., Pharmacol. Rew., (1993), 310–379). Both QUIN and KYNA are able to interact with the ionotropic excitatory amino acid receptors. In particular, QUIN is a highly selective agonist at the N-methyl-D-aspartate (NMDA) receptor (Stone T. W., Eur. J. Pharmacol., 72, (1981) 411–412), whereas KYNA is a broad spectrum antagonist of the ionotropic excitatory aminoacid receptors, preferentially acting at the glycine co-agonist site of the NMDA receptor (J. Neurochem., 52, (1989) 1319–1328).

In vitro studies have demonstrated that the exposure of neuronal cell cultures to relatively low QUIN concentrations are neurotoxic either when applied over a prolonged period of time or in combination with glutamate (Schurr A., Brain Res., 568, (1991) 199–204). In vivo QUIN has been shown to produce convulsions and axon sparing lesions that mimic the nerve cell loss described in human neurodegenerative disorders (Schwarcz R., Science, 219, (1983) 316–318). Moreover an increase in QUIN production has been demonstrated in postischemic gerbil brain (Saito K., J. Neurochem., 60, (1993) 180–192), following spinal cord trauma in rats (Stokes B. T., Brain Res., 633, (1994) 348–352) and in guinea pig (Blight A. R., Brain Res., 632, (1993) 314–316), and, finally, in a model of experimental allergic encephalomyelitis (Flagan E. M., J.Neurochem., 64, (1995) 1192–1196).

On the other hand, KYNA has shown anticonvulsant and neuroprotective properties in several animal models (Stone T. W. Pharmacol.Rev.45,(1993) 309–379), and, additionally, the experimentally-evoked rise of KYNA concentrations is capable to elicit neuroprotection and seizures reduction (Nozaki K., J. Cereb. Blood Flow Metab., (1992), 12, 400–407; Russi P., J. Neurochem., 59, (1992) 2076).

Notably, KYNA when co-injected with QUIN is able to prevent the excitotoxic neuronal damage evoked by the neurotoxin (Foster A. C., Neurosci. Lett., 48, (1984) 273–278). These data taken together show that KYNA may act as the brain's own defence against detrimental events, such as excitotoxicity and seizures, leading to pathological situations (Schwarcz R., Neurotoxin and neurodegenerative disease, Ann. N.Y.Sci., 140, vol. 648, 1992).

It follows that, pharmacological interventions aimed at increasing KYNA formation and/or blocking QUIN synthesis, can be useful for the therapy of excitotoxic brain diseases. Since in the kynurenine pathway (FIG. 1), KYN-3-OHase is the first enzyme involved in the formation of QUIN from KYN compounds which act as inhibitors of this enzyme are expected to block the metabolism toward QUIN and, at the same time, to increase KYNA formation.

Consequently, compounds able of inhibiting this enzyme are useful in the prevention and/or treatment of a variety of pathologies involving quinolinic acid or excessive activation of the neurotransmission mediated by excitatory amino acid receptors.

Accordingly, the present invention provides a 4-phenyl-4-oxo-2-butenoic acid derivative of formula (I) either as single isomer or as mixture of isomers wherein X, Y and Z are, each independently, hydrogen; halogen; nitro; $C_1$–$C_6$ alkyl; phenyl; benzyl; $C_1$–$C_6$ alkoxy; $C_1$–$C_6$ alkylthio; $SOR_5$, $SO_2R_5$ in which $R_5$ is $C_1$–$C_6$ alkyl, phenyl, benzyl, $C_2$–$C_4$ alkenyl or $C_2$–$C_4$ alkynyl; $SO_2N(R_6)_2$ in which each of $R_6$ is, independently, hydrogen, $C_1$–$C_6$ alkyl, $C_2$–$C_4$ alkenyl, $C_2$–$C_4$ alkynyl, phenyl or benzyl;

R is hydroxy; —$OR_5$ in which $R_5$ is as defined above; —$N(R_6)_2$ or —$N(R_6)OR_6$ in which $R_6$ is as defined above;

$R_1$ and $R_2$ are, each independently, hydrogen, halogen, hydroxy, $C_1$–$C_6$ alkoxy, $C_1$–$C_6$ alkyl, phenyl or benzyl; or a pharmaceutically acceptable salt thereof, for use in a method of treatment of the human or animal body by therapy.

Typically, the 4-phenyl-4-oxo-butenoic acid derivative is provided for use as a kynurenine-3-hydroxylase inhibitor.

In particular, the present invention relates to the use of a compound of formula (I) or a pharmaceutically acceptable salt thereof in the prevention and/or treatment of a neurodegenerative disease wherein the inhibition of the enzyme kynurenine-3-hydroxylase is needed.

More in particular, this invention refers to the use of a compound of formula (I) or a pharmaceutically acceptable salt thereof in the prevention and/or treatment of a neurodegenerative disease which comprises Huntington's chorea, Alzheimer's disease, dementia caused by acquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammations of the brain.

A preferred class of compounds of formula (I) according to the invention are compounds of formula (I) wherein R is hydroxy or —$OR_5$ in which $R_5$ is $C_1$–$C_6$ alkyl;

one of X, Y and Z is hydrogen and the other two are, each independently, hydrogen; halogen; nitro; $C_1$–$C_6$ alkyl; phenyl; benzyl; $C_1$–$C_6$ alkoxy, $C_1$–$C_6$ alkylthio; $SOR_5$, $SO_2R_5$ in which $R_5$ is $C_1$–$C_6$ alkyl, phenyl, benzyl, $C_2$–$C_4$ alkenyl or $C_2$–$C_4$ alkynyl; $SO_2N(R_6)_2$ in which each of $R_6$ is, independently, hydrogen, $C_1$–$C_6$ alkyl, $C_2$–$C_4$ alkenyl, $C_2$–$C_4$ alkynyl, phenyl or benzyl;

$R_1$ and $R_2$ are each independently, hydrogen, halogen, hydroxy, $C_1$–$C_6$ alkoxy, $C_1$–$C_6$ alkyl, phenyl or benzyl; and the pharmaceutically acceptable salts thereof.

Specific examples of preferred compounds of formula (I), either as single isomer or as mixture of isomers, are listed below:
4-(3'-bromophenyl)-4-oxo-2-butenoic acid;
4-(3',4'-dichlorophenyl)-4-oxo-2-butenoic acid;
4-(3',4'-difluorophenyl)-4-oxo-2-butenoic acid;
4-(3',4'-dibromophenyl)-4-oxo-2-butenoic acid;
4-(3'-chloro-4'-methoxyphenyl)-4-oxo-2-butenoic acid;
2-hydroxy-4-(4'-chlorophenyl)-4-oxo-2-butenoic acid;
2-hydroxy-4-(4'-fluorophenyl)-4-oxo-2-butenoic acid;
2-hydroxy-4-(4'-nitrophenyl)-4-oxo-2-butenoic acid;
2-hydroxy-4-(4'-methoxyhenyl)-4-oxo-2-butenoic acid;
Methyl 4-(3',4'-dichlorophenyl)-4-oxo-2-butenoate;
and the pharmaceutically acceptable salts thereof.

The present invention also refers to a selected class of 4-phenyl-4-oxo-2-butenoic acid derivatives of formula (I), as novel compounds.

Accordingly, the present invention provides a 4-phenyl-4-oxo-2-butenoic acid derivative of formula (IA) either as a single isomer or as a mixture of isomers (IA)

wherein

X is halogen; nitro; $SOR_5$, $SO_2R_5$ in which $R_5$ is $C_1$–$C_6$ alkyl benzyl, phenyl, $C_2$–$C_4$ alkenyl or $C_2$–$C_4$ alkynyl; or $SO_2N(R_6)_2$ in which each $R_6$ is, independently, hydrogen, $C_1$–$C_6$ alkyl, benzyl, phenyl or $C_2$–$C_4$ alkenyl;

Y is hydrogen; halogen; nitro; $C_1$–$C_6$ alkyl; $C_1$–$C_6$ alkoxy; $C_1$–$C_6$ alkylthio; $SOR_5$, $SO_2R_5$ in which $R_5$ is as defined above; or $SO_2N(R_6)_2$ in which $R_6$ is as defined above;

R is hydroxy; $OR_5$ in which $R_5$ is as defined above; $N(R_6)_2$ or $N(R_6)OR_6$ in which $R_6$ is as defined above;

$R_1$ and $R_2$ are, each independently, hydrogen, halogen, hydroxy, $C_1$–$C_6$ alkoxy, $C_1$–$C_6$ alkyl, phenyl or benzyl;

or a pharmaceutically acceptable salt thereof;
provided that:

(i) when Y and $R_2$ are both hydrogen and $R_1$ is methyl, X is not nitro;

(ii) when X is halogen and Y, in position 4' of the phenyl residue, is $C_1$–$C_4$ alkyl, $R_1$ and $R_2$ are not both hydrogen;

(iii) when X and Y, in position 4' of the phenyl residue, are both chloro, bromine or fluorine, $R_1$ and $R_2$ are not both hydrogen;

(iv) when X is chlorine and Y, in position 6' of the phenyl residue, is phenyl, methyl or methoxy, $R_1$ and $R_2$ are not both hydrogen;

(v) when X is chlorine and Y, in position 4' of the phenyl residue, is phenyl or methoxy, $R_1$ and $R_2$ are not both hydrogen;

(vi) when X is bromine and Y is in position 4' of the phenyl residue, Y, $R_1$ and $R_2$ are not simultaneously hydrogen; and (vii) when X and Y in position 4' of the phenyl residue are both chlorine, $R_1$ is not benzyl.

A preferred class of compounds of formula (IA) are compounds of formula (IA) wherein X is halogen or nitro;

Y is hydrogen, halogen or $C_1$–$C_6$ alkoxy;

R is hydroxy or —$OR_5$ in which $R_5$ is $C_1$–$C_6$ alkyl;

$R_1$ and $R_2$ are, each independently, hydrogen, halogen, hydroxy, $C_1$–$C_6$ alkoxy, $C_1$–$C_6$ alkyl, phenyl or benzyl, and the pharmaceutically acceptable salts thereof;
provided that:

(i) when Y and $R_2$ are both hydrogen and $R_1$ is methyl, X is not nitro;

(ii) when X is halogen and Y, in position 4' of the phenyl residue, is $C_1$–$C_4$ alkyl, $R_1$ and $R_2$ are not both hydrogen;

(iii) when X and Y, in position 4' of the phenyl residue, are both chlorine, bromine or fluorine, $R_1$ and $R_2$ are not both hydrogen;

(iv) when X is chlorine and Y, in position 6' of the phenyl residue, is phenyl, methyl or methoxy, $R_1$ and $R_2$ are not both hydrogen;

(v) when X is chlorine and Y, in position 4' of the phenyl residue, is phenyl or methoxy, $R_1$ and $R_2$ are not both hydrogen;

(vi) when X is bromine and Y is in position 4' of the phenyl residue, Y, $R_1$ and $R_2$ are not simultaneously hydrogen; and (vii) when X and Y in position 4' of the phenyl residue are both chlorine, $R_1$ is not benzyl.

Specific examples of preferred compounds of formula (IA) either as single isomer or as mixture of isomers, are listed below:
4-(3'-fluorophenyl)-4-oxo-2-butenoic acid;
4-(3'-chlorophenyl)-4-oxo-2-butenoic acid;
4-(3'-nitrophenyl)-4-oxo-2-butenoic acid;
4-(3'-fluoro-4'-methoxyphenyl)-4-oxo-2-butenoic acid;
2-methyl-4-(3',4'-dichlorophenyl)-4-oxo-2-butenoic acid;
3-methyl-4-(3',4'-dichlorophenyl)-4-oxo-2-butenoic acid;
3-phenyl-4-(3',4'-dichlorophenyl)-4-oxo-2-butenoic acid;
3-benzyl-4-(3',4'-dichlorophenyl)-4-oxo-2-butenoic acid;
2,3-dimethyl-4-(3',4'-dichlorophenyl)-4-oxo-2-butenoic acid;
2-hydroxy-4-(3'-chlorophenyl)-4-oxo-2-butenoic acid;
2-hydroxy-4-(3'-fluorophenyl)-4-oxo-2-butenoic acid;
2-hydroxy-4-(3',4'-dichlorophenyl)-4-oxo-2-butenoic acid;
2-hydroxy-4-(3',4'-difluorophenyl)-4-oxo-2-butenoic acid;
2-hydroxy-4-(3'-chloro-4'-methoxyphenyl)-4-oxo-2-butenoic acid;
and their pharmaceutically acceptable salts.

The present invention also provides a compound of formula (IA) for use in a method of treating the human or animal body by therapy.

Typically, a compound of formula (IA) is provided for use as a kynurenine-3-hydroxylase inhibitor.

The pharmaceutically acceptable salts of the compounds of formula (I) or (IA) include the salts with inorganic bases, which as, for example, hydroxides of alkali metals, e.g. sodium or potassium, or alkaline-heart metals, e.g. calcium or magnesium, and the salts with organic bases, such as, for example, aliphatic amines, e.g. methyl amine, ethyl amine, diethyl amine, or heterocyclic amines, e.g. piperidine.

With reference to both formulae (I) and (IA), the meaning of the various substituents are as follows. If not otherwise stated, the alkyl, alkoxy and alkylthio chains may be branched or straight chains.

Representative examples of $C_1$–$C_6$ alkyl chains include $C_1$–$C_4$ alkyl chains such as methyl, ethyl, n- and iso-propyl, n-, iso-, sec- and tert-butyl.

Representative examples of $C_1$–$C_6$ alkoxy groups include $C_1$–$C_4$ alkoxy groups such as methoxy and ethoxy.

Representative examples of $C_1$–$C_6$ alkylthio groups include $C_1$–$C_4$ alkylthio groups such as methylthio, ethyltio and isopropylthio.

A halogen atom is fluoro, bromo, chloro or iodo; in particular it is fluoro or chloro.

Representative examples of $C_2$–$C_4$ alkenyl group include vinyl and allyl.

Representative examples of $C_2$–$C_4$ alkynyl include ethynyl or propargyl.

The compounds of formula (I) or (IA) can be prepared by a process which comprises:

a) reacting a compound of formula (II)

(II)

wherein
X, Y and Z are, each independently, hydrogen, halogen, $C_1$–$C_6$ alkyl, phenyl, benzyl, $C_1$–$C_6$ alkoxy or $C_1$–$C_6$ alkylthio;
with a compound of formula (III)

(III)

wherein
$R_1$ and $R_2$ are, each independently, hydrogen $C_1$–$C_6$ alkyl, phenyl, benzyl or halogen, to obtain a compound of formula (I) or (IA) wherein X, Y, Z, $R_1$ and $R_2$ are as defined above and R is hydroxy; or b) reacting a compound of formula (IV)

(IV)

wherein
X, Y and Z are, each independently, hydrogen; halogen; nitro; $C_1$–$C_6$ alkyl; phenyl; benzyl; $C_1$–$C_6$ alkoxy; $C_1$–$C_6$ alkylthio; $SOR_5$ $SO_2R_5$ in which $R_5$ is $C_1$–$C_6$ alkyl, phenyl, benzyl, $C_2$–$C_4$ alkenyl or $C_2$–$C_4$ alkynyl; or $SO_2N(R_6)_2$ in which each $R_6$ is independently, hydrogen, $C_1$–$C_6$ alkyl, $C_2$–$C_4$ alkenyl, $C_2$–$C_4$ alkynyl, phenyl or benzyl; and
$R_2$ is hydrogen, $C_1$–$C_6$ alkyl, phenyl, benzyl, or $C_1$–$C_6$ alkoxy;
with a compound of formula (V)

(V)

wherein
W is hydrogen, hydroxy, $C_1$–$C_6$ alkyl or $C_1$–$C_6$ alkoxy; and
R is hydroxy or —$OR_5$ in which $R_5$ is $C_1$–$C_6$ alkyl; to obtain a compound of formula (I) or (IA) wherein X,Y,Z, $R_1$, $R_2$ and R are as defined above; and, if desired, c) converting a compound of formula (I) or (IA) so obtained under steps a) or b) into another compound of formula (I) or (IA) wherein $R_1$ and/or $R_2$ have/has different meaning; and/or if desired;

d) converting a compound of formula (I) or (IA) as obtained under steps a), b) or c) wherein R is hydroxy, into another compound of formula (I) or (IA) wherein R is other than hydroxy; and/or if desired;

e) converting a compound of formula (I) or (IA) into a pharmaceutically acceptable salts thereof or obtaining a free compound from the corresponding salt.

The reaction of a compound of formula (II) with a compound of formula (III) as described in step a), may be carried out according to known methods (Kazuya Kameo, Chem. Pharm. Bull., 36, 6, 2050–2060 (1988); Bianchi M., Eur.J.Med.Chem.,23,45–52 (1988).

For example, the reaction can be performed in the presence of a suitable Lewis acid catalyst, in an inert solvent such as, e.g., dichloromethane or 1,2-dichloroethane, or in an appropriate aromatic hydrocarbon such as, e.g., chlorobenzene, nitrobenzene or in an excess of the compound of formula (II) itself; at a temperature ranging from about −10° C. to about 100° C.; optionally in the presence of a co-solvent, e.g. nitromethane.

A suitable Lewis acid may be anhydrous aluminum trichloride, anhydrous tin dichloride, titanium tetrachloride or anhydrous zinc dichloride, typically anhydrous aluminum trichloride.

The compounds of formula (II) are known compounds.

The compounds of formula (III) are known compounds or can be prepared by known procedures from known compounds.

The reaction of a compound of formula (IV) with a compound of formula (V), as described in step b), can be carried out according to known methods (Witiak M., J Med. Chem., 14, 8, 758–766 (1971); Williams H. W. R., J. Med. Chem., 26,1196–1200 (1983); Wermuth C. G., Chim. Ther., 141–145 (1971); Tomassini J., Baldwin,J., M. Bourgeois, Antimicrob. Agents Chemother., 38, 2827–37 (1994).

For example, the reaction can be performed either using a suitable acid or basic catalyst such as, e.g., hydrochloric acid, sulfuric acid or sodium methoxyde, or without catalyst. Tipical solvents are, e.g., acetic acid, dioxane, toluene or benzene, or the reaction can be carried out in an excess of the compound of formula (IV) itself; the reaction temperature may range from about 50° C. to about 120° C.

The compound of formula (IV) are either known compounds or can be obtained from known compounds according to procedures well known in the art.

The conversion of a compound of formula (I) or (IA) in which R is hydroxy into another compound of formula (I) or (IA) in which R is not hydroxy, as described in step d), can be carried out according to know methods.

Thus, a compound of formula (I) or (IA) wherein R is hydroxy, can be converted into another compound of formula (I) or (IA) wherein R is —$OR_5$, in which $R_5$ is as defined above, by usual esterification methods. Esterification reactions can be carried out preferably via a reactive intermediate of the carboxylic acid, which may be isolated or not, by reaction with the appropriate alcohol of formula $R_5OH$ in which $R_5$ is as defined above. The reaction can be carried out in a customary solvent, e.g., dichloromethane, tetrahydrofuran, toluene, or in the presence of an excess of the alcohol itself. The reaction temperature may range from about –20° C. to about 50° C. Intermediate reactive derivatives of the carboxylic acid may be, for example, acid halides, e.g. the chloride, mixed anhydrides, e.g. ethoxycarbonyl or isobutyloxycarbonyl anhydride, or a suitable reactive intermediate obtained "in situ", e. g., by reaction with a diimide, e.g., dicychloexylcarbodiimide or carbonyl diimidazole. The esterification reaction may be also carried out by treatment of the compound of formula (I) or (IA) with a suitable alkylating agent of formula $R_5$—X, wherein $R_5$ is as defined above, and X an appropriate leaving group such as, e.g. halogen atom, preferably iodine, or a sulfate ester, in the presence of an inorganic base, e.g. potassium carbonate or bicarbonate, or in the presence of an organic base, e.g. diazabicycloundecene (DBU), in a suitable solvent, e.g. dimethylformamide, at a reaction temperature that may range from about 0° C. to about 60° C.

Furthermore, a compound of formula (I) or (IA) wherein R is hydroxy can be converted into a corresponding compound of formula (I) or (IA) wherein R is —$N(R_6)_2$ or —$N(R_6)$ $OR_6$, wherein $R_6$ is as defined above, according to known methods; preferably, via an intermediate reactive derivative thereof which can be isolated or not. Intermediate derivatives may be active esters, e.g., $NO_2$-phenyl esters or N-hydroxysuccinimide esters; acid halides, preferably chlorides; mixed anhydrides, e.g. ethoxycarbonyl or isobutyloxycarbonyl anhydrides; or reactive intermediates obtained "in situ" by reaction of the acid with diciclohexylcarbodiimide or carbonyl-diimidazole. For example, a reactive intermediate as defined above, obtainable following conventional ways, usually employed in the synthesis of peptides, is reacted with ammonia or an appropriate amine $HN(R_6)_2$ in which each $R_6$ is as defined above, or reacted with an hydroxylamine or a protected hydroxylamine $HN(R_6)O$—$R_7$ wherein $R_7$ is $C_1$–$C_6$ alkyl, benzyl or a protecting group; in the last case, $R_7$ is, preferably, benzyl or trialkyl-silyl. The reaction solvent may be a customary solvent, e.g., dichloromethane, tetrahydrofuran, dioxane or an excess of the amine itself, and the reaction temperature may range from about –20° C. to about 50° C.

The optional salification of a compound of formula (I) or (IA) as well as the conversion of a salt into the free compound and the separation of a mixture of E/Z geometric isomers as described in step e) into the single isomers may be carried out by conventional methods. Particularly, the separation either of regioisomers or of E/Z geometrical isomers may be carried out by fractional crystallization from a suitable solvent or by chromatography, either flash column chromatography or high pressure liquid chromatography.

As already said, the compounds of formula (IA) represent a selected class of compounds of formula (I) and are thus effective in the prevention and/or treatment of all the disease for which the compounds of formula (I) have been indicated as therapeutic agents.

Accordingly, the compounds of formula (IA) are useful as kynurenine-3-hydroxylase inhibitors; in particular, they are useful in the prevention and/or treatment of a neurodegenerative disease wherein the inhibition of the enzyme kynurenine-3-hydroxylase is needed.

More in particular, the compounds of formula (IA) can be useful in the prevention and/or treatment of a neurodegenerative disease which comprises: Huntington's chorea, Alzheimer's disease, dementia caused by acquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammation of the brain.

A human or animal may thus be treated by a method which comprises the administration of a pharmaceutically effective amount of a compound of formula (I) or (IA) or salt thereof.

The efficacy of the compounds of formula (I) or (IA) in the inhibition of the enzyme kynurenine-3-hydroxylase has been evaluated both in rat brain homogenate and in rat liver homogenate, determining the conversion of L-kynurenine to L-3-hydroxy-kynurenine according to the methods described below.

Kynurenine-3-hydroxylase Assay in the Rat Brain

Brain was homogenized in ice-cold 0.32 M sucrose and centrifuged at 12000×g for 30 min at 4° C. The pellet was washed three times with 0.32 M sucrose by centrifugation and suspended in 0.14 M KCl in 20 mM K-phosphate buffer at pH 7 (1 g tissue in 2 ml buffer).

The reaction mixture contained: 75 µl of suspended homogenate; 100 µl of substrate solution containing 50 mM K-phosphate buffer pH 7.5, 2 mM $MgCl_2$, 0.4 mM NADPH, 50 µM L-kynurenine (final concentration), and 25 µl of different concentrations of inhibitor solutions. The reaction was stopped by addition of 200 µl of 1 M $HClO_4$ after 60 min incubation. L-3-hydroxykynurenine formed was quantified by HPLC with coulometric detection at a working voltage of +0.2 V. The column was a 10 cm $C_{18}$ reversed phase (3 µm. The mobile phase consisted of 950 ml distilled water, 20 ml acetonitrile, 9 ml triethylamine, 5.9 ml phosphoric acid, 100 mg sodium EDTA and 1.5 g heptanesulfonic acid. The flow rate was 1 ml/min.

Kynurenine-3-hydroxylase Assay in the Rat Liver

The efficacy of the compounds of formula (I) in the inhibition of the enzyme kynurenine-3-hydroxylase has been evaluated in rat liver mitochondrial extract as reported below, according to known methods (A Radiometric Assay for Kynurenine 3-Hydroxylase Based on the Release of $^3H_2O$ during Hydroxylation of L-(3,5-$^3$H)Kynurenine; Joel B.Erickson, Ellen M.Flanagan, Suzanne Russo, and John F.Reinhard.Jr.; Analytical Biochem. (1992), 205, 257–262) with minor modifications.

The assay for kynurenine 3-hydroxylase was based on the enzymatic synthesis of tritiated water during the hydroxylation reaction. Radiolabeled water was quantified following selective adsorption of the isotopic substrate and its metabolite with activated charcoal.

Rat liver mitochondrial extract was used as enzymatic preparation for this assay.

The assay for kynurenine 3-hydroxylase activity was carried out at 37° C. for a time of 30 min. The reaction mixture of a total volume of 100 ml was constituted of 44 mg of suspended extract, 100 mM Tris/Cl⁻buffer pH 8.1, 10 mM EDTA, 100 mM KCl, 0.8 mM NADPH, 0.025 mM L-kynurenine, 0.5 mCi L-(3,5-$^3$H)Kynurenine (10 Ci/mmol) and 10 ml of different concentration of inhibitor solutions. After the incubation the reaction was terminated by the addition of 1 mL of 7.5% (w/v) activated charcoal, vortexed and centrifugated for 7 min.

A 500 ml aliquot of supernatant was counted by scintillation spectroscopy in 5 ml of liquid scintillation.

As an example, the compounds of the present invention:
(E)-4-(3',4'-dichlorophenyl)-4-oxo-2-butenoic acid (internal code: PNU 157694)
(E)-4-(3',4'-difluorophenyl)-4-oxo-2-butenoic acid (internal code: PNU 157961)
(E)-4-(3'-fluorophenyl)-4-oxo-2-butenoic acid (internal code: PNU 158388);
(E)-4-(3'-chlorophenyl)-4-oxo-2-butenoic acid (internal code: PNU 158390);
(E)-4-(3'-nitrophenyl)-4-oxo-2-butenoic acid (internal code: PNU 158389);
(E)-2-methyl-4-(3',4'-dichlorophenyl)-4-oxo-2-butenoic acid (internal code: PNU 158785);
3-methyl-4-(3',4'-dichlorophenyl)-4-oxo-2-butenoic acid (internal code: PNU 161213);
3-benzyl-4-(3',4'-dichlorophenyl)-4-oxo-2-butenoic acid (internal code: PNU 167535);
(E)-2-hydroxy-4-(3'-chlorophenyl)-4-oxo-2-butenoic acid (internal code: PNU 161216);
(E)-2-hydroxy-4-(3'-fluorophenyl)-4-oxo-2-butenoic acid (internal code: PNU 161217);
(E)-2-hydroxy-4-(4'-chlorophenyl)-4-oxo-2-butenoic acid (PNU 166909);
(E)-2-hydroxy-4-(3',4'-dichlorophenyl)-4-oxo-2-butenoic acid (internal code: PNU 158776);
(E)-2-hydroxy-4-(3',4'-difluorophenyl)-4-oxo-2-butenoic acid (internal code: PNU 161219);
Methyl-(E)-2-hydroxy-4-(3',4'-dichlorophenyl)-4-oxo-2-butenoate (internal code: PNU 158775); and
Ethyl-(E)-2-hydroxy-4-(3',4'-dichlorophenyl)-4-oxo-2-butenoate (internal code: PNU 161215);
have been tested according to the methods described above. The obtained results are reported in the following Table 1

TABLE 1

| Enzyme Inhibition Compound | (Brain) IC$_{50}$ (µM) | (Liver) IC$_{50}$ (µM) |
|---|---|---|
| PNU 157694 | 0.9 | 10.4 |
| PNU 157961 | 1.1 | 21.1 |
| PNU 158388 | 21.8 | 38.6 |
| PNU 158389 | 16.6 | 30.4 |
| PNU 158390 | 20.4 | 21.9 |
| PNU 158785 | 3.4 | 23.5 |
| PNU 161213 | — | 26.2 |
| PNU 167535 | — | 12.3 |
| PNU 161216 | 6.9 | 1.2 |
| PNU 161217 | 0.97 | 2.8 |
| PNU 166909 | — | 8.9 |
| PNU 158776 | 0.3 | 1.8 |
| PNU 161219 | 0.44 | 1.2 |
| PNU 158775 | 0.95 | 6.9 |
| PNU 161215 | 2.01 | 1.9 |

The tested compounds were found to be significantly active in inhibiting the enzyme kynurenine-3-hydroxylase.

The compounds of the invention can be administered in a variety of dosage forms, e.g. orally, in the form of tablets, capsules, sugar or film coated tablets, liquid solutions or suspensions; parenterally, e.g. intramuscolarly or by intravenous injection or infusion.

The dosage level suitable for administration to adult humans depends on the age, weight, conditions of the patient and on the administration route; for example, the dosage adopted for oral administration for the compounds of the invention may range from about 10 to about 500 mg pro dose, from 1 to 5 times daily.

The present invention also provides pharmaceutical compositions comprising a compound of formula (I) or (IA) as an active ingredient in association with a pharmaceutically acceptable excipient (which can be a carrier or a diluent).

Furthermore the present invention provides pharmaceutical compositions comprising a compound of formula (I) as an active ingredient in association with a pharmaceutically acceptable excipient (which can be a carrier or a diluent) for use as kynurenine 3-hydroxylase inhibitor).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscolar injections may contain, together with the active compound, a pharmaceutically acceptable carrier, e.g. sterile water, olive oil, ethyl oleate, glycols, e.g. propylene glycol, and, if desidered, a suitable amount of lidocaine hydrochloride. The solutions for intravenous injections or infusions may contain as carrier, for example, sterile water or preferably they may be in the form of sterile, acqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the invention.

EXAMPLE 1

(E)-4-(3',4'-difluorophenyl)-4-oxo-2-butenoic acid (PNU 1157961)

Aluminum chloride anhydrous (32.6 g, 0.245 mol.) was added at room temperature and under dry nitrogen atmosphere, to a solution of maleic anhydride (9.6 g, 0.098 mol.) and difluorobenzene (20 ml, 0.195 mol.) in dry dichloromethane. The reaction mixture was heated to reflux for 4 hours; then cooled and quenched with ice/37% hydrochloric acid (100 g/100 mL). Dichloromethane (200 mL) was added, the phases separated and the aqueous layer was extracted twice with dichloromethane (50 mL), the collected organic extracts were washed with 2N HCl and then with brine. The resulting solution was dried ($Na_2SO_4$) and evaporated in vacuo to provide the crude product, as deep yellow oily material, which was dissolved in diethyl ether (60 mL). The organic phase was extracted with saturated sodium bicarbonate solution (150 mL), the collected aqueous layers were washed with diethyl ether and cooled at 0° C., then to the alkaline aqueous solution, 37% hydrochloric acid was added on stirring until the pH was 2. The obtained suspension was extracted with ethyl acetate (3×100 mL); the collected organic extracts were washed with brine, dried ($Na_2SO_4$) and evaporated in vacuo to provide a yellow solid (11 g). Crystallisation from toluene provided the pure titled compound (7.6 g, 40%) melting at 107–108° C.

| Calcd. for $C_{10}H_6F_2O_3$ | : | C | 56.61 | ; | H | 2.85 |
| --- | --- | --- | --- | --- | --- | --- |
| Found | : | | 57.85 | ; | | 3.07 |

MS (EI) m/z 212.0 (M$^{+\cdot}$); 141.1. $^1$H-NMR (d$_6$-DMSO, 200 MHz) ppm: 6.68 (1H, d, J=15.4 Hz); 7.60 (1H, t); 7.78 (1H, d); 7.85 (1H, d, J=15.4 Hz); 8.05 (2H, m), 13.20 (1H, broad s).

Analogously, the following compounds can be prepared:
(E)-4-(3',4'-dichlorophenyl)-4-oxo-2-butenoic acid (RN: 80937-20-8)(PNU 157694)
mp. 146–47° C. (lit.: 141–44° C.);

| Calcd. for $C_{10}H_6Cl_2O_3$ | : | C | 48.98 | ; | H | 2.45 | ; | Cl | 28.98 |
| --- | --- | --- | --- | --- | --- | --- | --- | --- | --- |
| Found | : | | 48.56 | ; | H | 2.57 | ; | | 28.48 |

MS (EI) m/z: 244.0 (M$^{+\cdot}$); 173.0 ($C_6H_3Cl_2CO$)$^+$. $^1$H-NMR (d$_6$-DMSO, 200 MHz) ppm: 6.72 (1H, d, J=15.4 Hz); 7.76 (1H, d); 7.80 (1H, d, J=15.4 Hz); 7.95 (1H, dd); 8.18 (1H, d), 13.10 (1H, broad s);
(E)-4-(3',4'-dibromophenyl)-4-oxo-2-butenoic acid;
(E)-4-(3'-chloro-4'-methoxyphenyl)-4-oxo-2-butenoic acid;
(E)-4-(3'-fluoro-4'-methoxyphenyl)-4-oxo-2-butenoic acid, and 2,3-dimethyl-4-(3',4'-dichlorophenyl)-4-oxo-2-butenoic acid.

EXAMPLE 2
(E)-4-(3'-chlorophenyl)-4-oxo-2-butenoic acid (PNU 158390)

A stirred mixture of 3'-Chloroacetophenone (15 mL, 97 mmol) and glyoxylic acid monohydrate (9 g, 97 mmol) was heated at 130° C. under reduced pressure (1,5 mmHg), over 8 hours. During this time the reduced pressure was maintained in order to remove the water formed during the reaction. After cooling, the crude reaction product was taken up in aqueous 10% potassium carbonate solution (100 mL) and the resulting solution was washed with diethyl ether (3×30 mL), the alkaline aqueous layer was cooled at 0° C. and then cautiously acidified with 6N HCl. The resulting suspension was extracted with ethyl acetate (3×50 mL), the collected organic extracts were washed with brine and dried ($Na_2SO_4$). Concentration of the solvent in vacuo afforded a yellow solid (8 g) which was chromatographed ($SiO_2$;$CH_2Cl_2$/MeOH 98:2) to provide the pure acid (6 g, 30%), lightly yellow solid melting at 158–59° C. (diisopropyl ether).

| Calcd. for $C_{10}H_7ClO_3$ | : | C | 57.00 | ; | H | 3.35 | ; | Cl | 16.86 |
| --- | --- | --- | --- | --- | --- | --- | --- | --- | --- |
| Found | : | | 56.93 | ; | | 3.40 | ; | | 17.01 |

MS (FD) m/z: 210 (M$^{+\cdot}$) $^1$H-NMR (d$_6$-DMSO, 200 MHz) ppm: 6.68 (1H, d, J=15.6 Hz); 7.50–1.70 (1H, m); 7.84 (1H, d, J=15.6 Hz); 7.87–8.10 (2H, m), 13.20 (1H, broad s).

Analogously, using the appropriate acetophenones, the following compounds can be prepared:
(E)-4-(3'-nitrophenyl)-4-oxo-2-butenoic acid (PNU 158389): mp. 178–79° C.

| Calcd. for $C_{10}H_7NO_5$ | : | C | 54.29 | ; | H | 3.19 | ; | N | 6.33 |
| --- | --- | --- | --- | --- | --- | --- | --- | --- | --- |
| Found | : | | 53.46 | ; | | 3.26 | ; | | 6.20 |

MS (FD) m/z: 221 (M$^{+\cdot}$) $^1$H-NMR (d$_6$-DMSO, 200 MHz) ppm: 6.66 (1H, d, J=15.5 Hz); 7.83 (1H, m); 7.85 (1H, d, J=15.5 Hz ); 8.48 (2H, dt); 8.63 (1H,s);
(E)-4-(3'-fluorophenyl)-4-oxo-2-butenoic acid (PNU 158388): mp. 110–111° C. (Diethyl ether/hexane),

| Calcd. for $C_{10}H_7FO_3$ | : | C | 61.85 | ; | H | 3.64 ; |
| --- | --- | --- | --- | --- | --- | --- |
| Found | : | | 61.13 | ; | | 3.72 ; |

MS (FD) m/z: 194 (M)$^{+\cdot}$. $^1$H-NMR (d$_6$-DMSO, 200 MHz) ppm: 6.78 (1H, d, J=15.6 Hz); 7.40–7.70 (3H, m); 7.83 (1H, d, J=15.5 Hz ); 7.78–7.90 (1H, m); 13.10 (1H, broad s); and
(E)-4-(3'-fluoro-4'-nitrophenyl)-4-oxo-2-butenoic acid.

Analogously, using the appropriate ketones, the following compounds can be prepared:
3-Methyl-4-(3',4'-dichlorophenyl)-4-oxo-2-butenoic acid (PNU 161213): prepared from 3,4-dichloropropiophenone in 65% yield, colorless plates, mp.143–144° C. (Toluene).

| Calcd. for $C_{11}H_8Cl_2O_3$ | : | C | 50.99 | ; | H | 3.11 | ; | Cl | 27.37 |
| --- | --- | --- | --- | --- | --- | --- | --- | --- | --- |
| Found | : | | 51.26 | ; | | 3.18 | ; | | 26.93 |

MS, EI (m/z): 258.0 (M)$^{+\cdot}$; 223.0 (M—Cl$^\cdot$)$^+$; 205.0 (M—Cl$^\cdot$—$H_2O$)$^+$; 172.9 ($C_6H_3Cl_2CO$)$^+$. $^1$H-NMR (200 MHz; d$_6$-DMSO), ppm: 2.20 (3H, s); 6.08 (1H,s); 7.63(1H, dd); 7.75 (1H, d); 7.90 (1H,d);
3-Phenyl-4-(3',4'-dichlorophenyl)-4-oxo-2-butenoic acid (PNU 167534): prepared from 1-(3',4'-dichlorophenyl)-2-phenyl-ethanone (mp.80–81° C.,hexane) in 40% yield; pale yellow needles, mp.101–103° C. (diethyl ether/hexane).

| Calcd. for $C_{16}H_{10}Cl_2O_3$ | : | C | 59.86 | ; | H | 3.14 | ; | Cl | 22.09 |
| --- | --- | --- | --- | --- | --- | --- | --- | --- | --- |
| Found | : | | 60.21 | ; | | 3.18 | ; | | 21.59; | and
3-Benzyl-4-(3',4'-dichlorophenyl)-4-oxo-2-butenoic acid (PNU 167535): prepared from 1-(3',4'-dichlorophenyl)-3-phenyl-propanone (colorless oil) in 46% yield; pale yellow needles, mp.154–156° C. (diisopropyl ether/hexane).

| Calcd. for C<sub>7</sub>H<sub>12</sub>Cl<sub>2</sub>O<sub>3</sub> | : | C | 60.95 | ; | H | 3.61 | ; | Cl | 21.17 |
|---|---|---|---|---|---|---|---|---|---|
| Found | : | | 61.07 | ; | | 3.78 | ; | | 20.96. |

Analogously, using pyruvic acid instead of glyoxylic acid the following compound can be prepared:

2-Methyl-4-(3',4'-dichlorophenyl)-4-oxo-2-butenoic acid (PNU 158785): Colorless prisms, mp. 153–154° C. (diisopropyl ether/hexane).

| Calcd. for $C_{11}H_8Cl_2O_3$ | : | C | 50.99 | ; | H | 3.11 | ; | Cl | 27.37 |
|---|---|---|---|---|---|---|---|---|---|
| Found | : | | 51.16 | ; | | 3.26 | ; | | 26.82 |

MS, EI (m/z): 260.0 (M)$^{+\cdot}$; 223.0 (M—Cl$^\cdot$)$^+$; 213.0 (M—COOH)$^+$; 205.0 (M—Cl$^\cdot$—H$_2$O)$^+$; 173.0 (C$_6$H$_3$Cl$_2$CO)$^+$. $^1$H-NMR (200 MHz; d$_6$-DMSO), ppm: 2.00 (3H, s); 7.60 (1H,s); 7.56(1H,d); 7.65 (1H, dd); 8.04 (1H,d); 13.20 (1H, broad s).

EXAMPLE 3

Methyl 2-hydroxy-4-(3',4'-dichlorophenyl)-4-oxo-2-butenoate (PNU 158775)

To a well stirred suspension of freshly prepared sodium ethylate (820 mg, 12 mmol) in dry benzene (10 mL), 3,4-dichloroacetophenone (1.89 g, 10 mmol) and dimethyloxalate (1.18 g, 10 mmol) dissolved in dry benzene (20 mL), were added dropwise on cooling at +5° C., and under dry nitrogen atmosphere. The resulting dark red suspension was stirred at room temperature over 4 hours. The reaction mixture was then poured into ice/2N HCl (1:1 w/w), stirred for 5 minutes and extracted with ethyl acetate. The combined organic extracts were washed with brine, dried and concentrated in vacuo to afford a pale yellow solid, which was recrystallized from acetonitrile to yield the pure ester (2.4 g, 86%), colorless needles, mp. 122–123° C.

| Calcd. for $C_{11}H_8Cl_2O_4$ | : | C | 48.03 | ; | H | 2.93 | ; | Cl | 25.78 |
|---|---|---|---|---|---|---|---|---|---|
| Found | : | | 48.11 | ; | | 3.06 | ; | | 26.12 |

MS, EI (m/z): 274.0 (M)$^{+\cdot}$; 215.0 (M—COOCH$_3$)$^+$; 173.0 (C$_6$H$_3$Cl$_2$CO)$^+$. $^1$H-NMR (200 MHz; d$_6$-DMSO), ppm: 3.9 (3H, s); 7.09 (1H,s); 7.79 (1H, d); 7.98 (dd, 1H); 8.22 (1H, d).

Analogously, starting from diethyl oxalate and the appropriate acetophenone the following compounds can be prepared:

Ethyl 2-hydroxy-4-(3',4'-dichlorophenyl)-4-oxo-2-butenoate (PNU 161215): colorless needles, mp. 59–61° C.

| Calcd. for $C_{12}H_{10}Cl_2O_4$ | : | C | 49.85 | ; | H | 3.49 | ; | Cl | 24.53 |
|---|---|---|---|---|---|---|---|---|---|
| Found | : | | 49.85 | ; | | 3.48 | ; | | 24.59 |

MS, EI (m/z): 288.0 (M); 215.0 (M—COOCH$_3$)$^{+\cdot}$; 173.0 (C$_6$H$_3$Cl$_2$CO)$^+$. $^1$H-NMR (200 MHz; d$_6$-DMSO), ppm: 1.23 (3H, t); 4.28 (2H, q) 7.09 (1H,s); 7.79 (1H, d); 7.98 (dd, 1H); 8.22 (1H, d);

Ethyl 2-hydroxy-4-(3'-chlorophenyl)-4-oxo-2-butenoate: colorless needles, mp. 57–58° C.

| Calcd. for $C_{12}H_{10}ClO_4$ | : | C | 56.63 | ; | H | 4.36 | ; | Cl | 13.95 |
|---|---|---|---|---|---|---|---|---|---|
| Found | : | | 56.65 | ; | | 4.41 | ; | | 14.00; |

Ethyl 2-hydroxy-4-(4'-chlorophenyl)-4-oxo-2-butenoate: colorless needles, mp. 59–61° C.

| Calcd. for $C_{12}H_{10}ClO_4$ | : | C | 56.63 | ; | H | 4.36 | ; | Cl | 13.95 |
|---|---|---|---|---|---|---|---|---|---|
| Found | : | | 56.70 | ; | | 4.44 | ; | | 13.95; |

Ethyl 2-hydroxy-4-(3'-fluorophenyl)-4-oxo-2-butenoate: colorless needles, mp. 56–57° C.

| Calcd. for $C_{12}H_{10}FO_4$ | : | C | 60.55 | ; | H | 4.66 |
|---|---|---|---|---|---|---|
| Found | : | | 60.52 | ; | | 4.70 |

MS, EI (m/z): 238(M)$^{+\cdot}$; 165 (M—COOCH$_2$CH$_3$)$^+$; 123 (C$_6$H$_3$FCO)$^+$. $^1$H-NMR (200 MHz; d$_6$-DMSO), ppm: 1.23 (3H, t); 4.32 (2H, q) 7.09 (1H,s); 7.43–7.61(2H,m); 7.80–7.93 (2H,m); and Ethyl 2-hydroxy-4-(3',4'-difluorophenyl)-4-oxo-2-butenoate: colorless needles, mp. 69–70° C.

| Calcd. for $C_{12}H_{10}FO_4$ | : | C | 56.30 | ; | H | 3.94 |
|---|---|---|---|---|---|---|
| Found | : | | 56.30 | ; | | 3.98 |

$^1$H-NMR (200 MHz; d$_6$-DMSO), ppm: 1.23 (3H, t); 4.38 (2H, q) 7.11 (1H,s); 7.50–7.68(1H,m); 7.91–8.02 (1H,m); 8.08–8.18 (1H, m).

EXAMPLE 4

2-Hydroxy-4-(3',4'-dichlorophenyl)-4-oxo-2-butenoic acid (PNU 158776)

To an ice cooled solution of Methyl 2-hydroxy-4-(3',4'-dichlorophenyl)-4-oxo-2-butenoate (1 g, 3.6 mmol) in 95% ethanol (120 mL), 1N sodium hydroxide (7.2 mL, 7.2 mmol) were added on stirring, the resulting mixture was stirred at 0° C. for 2 hours and at room temperature for further 3 hours. The most of solvent was removed under reduced pressure and the residue taken up with 2 N HCl, the resulting suspension was stirred for 5 minutes and then filtered. The solid was washed with water, dried and recrystallized from methanol to provide the pure acid as colourless prisms (845 mg, 90%), mp.180–181° C.

| Calcd. for $C_{10}H_6Cl_2O_4$ | : | C | 46.01 | ; | H | 2.32 | ; | Cl | 27.16 |
|---|---|---|---|---|---|---|---|---|---|
| Found | : | | 46.13 | ; | | 2.43 | ; | | 27.60 |

MS, EI (m/z): 260.0 (M)$^{+\cdot}$; 215.0 (M—COOCH$_3$)$^+$; 173.0 (C$_6$H$_3$Cl$_2$CO)$^+$. $^1$H-NMR (200 MHz; d$_6$-DMSO), ppm: 7.09 (1H,s); 7.80 (1H, d); 8.00 (dd, 1H); 8.27 (1H, d).

Analogously, the following compounds can be obtained from the corresponding ethyl esters:

2-Hydroxy-4-(3'-chlorophenyl)-4-oxo-2-butenoic acid (PNU161216): colorless solid, mp.169–170° C.

| Calcd. for $C_{10}H_7ClO_4$ | : | C | 53.00 | ; | H | 3.11 | ; | Cl | 15.64 |
|---|---|---|---|---|---|---|---|---|---|
| Found | : |  | 52.63 | ; |  | 3.65 | ; |  | 15.62 |

MS, EI (m/z): 226 (M)$^{+\cdot}$; 181 (M—COOH)$^+$; 139 ($C_6H_4ClCO$)$^+$. $^1$H-NMR (200 MHz; $d_6$-DMSO), ppm: 7.09 (1H,s); 7.60 (1H, t); 7.88 (1H, m); 8.02 (2H,m);

2-Hydroxy-4-(4'-chlorophenyl)-4-oxo-2-butenoic acid (PNU 166909): colorless needles, mp. 169–170° C.

| Calcd. for $C_{10}H_7ClO_4$ | : | C | 53.02 | ; | H | 3.11 | ; | Cl | 15.67 |
|---|---|---|---|---|---|---|---|---|---|
| Found | : |  | 52.42 | ; |  | 3.13 | ; |  | 14.87 |

MS, EI (m/z): 226 (M)$^{+\cdot}$; 181 (M—COOH)$^+$; 139 ($C_6H_4ClCO$)$^+$. $^1$H-NMR (200 MHz; $d_6$-DMSO), ppm: 6.50 (1H,s); 7.50 (2H, d); 7.88 (2H,dm);

2-Hydroxy-4-(3'-fluorophenyl)-4-oxo-2-butenoic acid (PNU 161217): colorless prisms, mp. 134–135° C.

| Calcd. for $C_{10}H_7FO_4$ | : | C | 57.15 | ; | H | 3.36 |
|---|---|---|---|---|---|---|
| Found | : |  | 57.04 | ; |  | 3.66 |

MS, EI (m/z): 210.0 (M)$^{+\cdot}$; 165.0 (M—COOH)$^+$; 123 ($C_6H_4FCO$)$^+$. $^1$H-NMR (200 MHz; $d_6$-DMSO), ppm: 7.85 (1H,s); 7.45–7.85(4H, m); and 2-Hydroxy-4-(3',4'-difluorophenyl)-4-oxo-2-butenoic acid (PNU 161219): colorless solid, mp. 163–166° C.

| Calcd. for $C_{10}H_6F_2O_4$ | : | C | 52.64 | ; | H | 2.65 |
|---|---|---|---|---|---|---|
| Found | : |  | 52.68 | ; |  | 2.82 |

MS, EI (m/z): 228.0 (M)$^{+\cdot}$; 183.0 (M—COOH)$^+$; 141 ($C_6H_4F_2CO$)$^+$. $^1$H-NMR (200 MHz; $d_6$-DMSO), ppm: 7.55 (1H,s); 7.50–7.62 (1H, m); 7.90–8.0 (1H, m); 8.04–8.18(1H, m).

EXAMPLE 5
(E)-Methyl-4-(3',4'-dichlorophenyl)-4-oxo-2-butenoate (PNU 158777)

To an ice cooled solution of (E)-4-(3',4'-dichlorophenyl)-4-oxo-2-butenoic acid (2.4 g, 0.01 mol) in dry DMF (80 mL), DBU (1.5 mL, 0.01) was added dropwise on stirring, under nitrogen atmosphere. To the resulting stirred solution iodomethane (3.1 mL, 0.05 mol) dissolved in dry DMF (20 mL) was added dropwise over 20 min. The resulting solution was stirred at 0° C. for 1 hour and 3 hours at room temperature. The resulting reaction mixture was poured into ice-water on stirring, and the precipitate was filtered, washed with water and then with hexane. Recrystallization from diisopropyl ether/hexane provided the pure ester (2.2 g, 86%), pale yellow needles, mp. 108–109°.

| Calcd. for $C_{11}H_8Cl_2O_3$ | : | C | 50.99 | ; | H | 3.11 | ; | Cl | 27.37 |
|---|---|---|---|---|---|---|---|---|---|
| Found | : |  | 51.13 | ; |  | 3.15 | ; |  | 27.39 |

MS, EI (m/z): 258.0 (M)$^{+\cdot}$; 227.0 (M—OCH$_3$)$^+$; 173.0 ($C_6H_3Cl_2CO$)$^+$. $^1$H-NMR (200 MHz; $d_6$-DMSO), ppm: 3.78 (3H, s); 6.78 (1H, d); 7.83 (1H,d); 7.95 (1H, d); 8.00 (dd, 1H); 8.23 (1H, d).

EXAMPLE 6
Capsule, each weighing 0.23 g and containing 50 mg of the active substance can be prepared as follows: Composition for 500 capsules:

| (E)-4-(3',4'-dichlorophenyl)-4-oxo-2-butenoic acid | 25 g |
|---|---|
| Lactose | 80 g |
| Corn starch | 5 g |
| Magnesium stearate | 5 g |

This formulation can be incapsulated in two hard gelatin capsules of two pieces, each with each capsule weighing 0.23 g.

EXAMPLE 7.
Intramuscular injection of 50 mg/ml

A pharmaceutical injectable composition can be manifactured dissolving 50 g (E)-4-(3',4'-dichlorophenyl)-4-oxo-2-butenoic acid in sterile propyleneglycol (1000 ml) and sealed in 1–5 ml ampoules.

Legend to FIG. 1:KYNURENINE PATHWAY
IDO:Indolamineoxygenase,
KYN:kynurenine
KYN-3-OHase:Kynurenine-3-hydroxylase
KYN-3-OH:3-hydroxy kynurenine—
KAT:Kynurenine amino transferase
3-OHAA:3-hydroxy anthranilic acid
KYNase:Kynureninase
3-HAO 3-hydroxy anthranilic acid dioxygenase
KYNA Kynurenic acid
QUIN quinolinic acid
TDO:tryptophanedioxygenase

We claim:

1. Method for treatment of a neurodegenerative disease by inhibiting the enzyme kynurenine-3-hydroxylase, comprising: administering to a patient in need thereof an effective amount of a compound of formula (I) either as a single isomer or as a mixture of isomers (I)

wherein

X, Y and Z are, each independently, hydrogen; halogen; nitro; $C_1$–$C_6$ alkyl; phenyl; benzyl; $C_1$–$C_6$ alkoxy; $C_1$–$C_6$ alkylthio; $SOR_5$, $SO_2R_5$ in which $R_5$ is $C_1$–$C_6$ alkyl, phenyl, benzyl, $C_2$–$C_4$ alkenyl or $C_2$–$C_4$ alkynyl; $SO_2N(R_6)_2$ in which each of $R_6$ is, independently, hydrogen, $C_1$–$C_6$ alkyl, $C_2$–$C_4$ alkenyl, $C_2$–$C_4$ alkynyl, phenyl or benzyl;

R is hydroxy; —$OR_5$ in which $R_5$ is as defined above; —$N(R_6)_2$ or —$N(R_6)OR_6$ in which $R_6$ is as defined above;

$R_1$ and $R_2$ are, each independently, hydrogen, halogen, hydroxy, $C_1$–$C_6$ alkoxy, $C_1$–$C_6$ alkyl, phenyl or benzyl; or a pharmaceutically acceptable salt thereof.

2. The method of claim 1, wherein the neurodegenerative disease is Huntington's chorea, Alzheimer's disease, dementia caused by acquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammations of the brain.

3. A pharmaceutical composition for treatment of a neurodegenerative disease in which the inhibition of the enzyme kyaurenine-3-hydroxylase is needed, comprising: a carrier and an effective amount of a 4-phenyl-4-oxo-2-butenoic acid compound of formula (IA) either as a single isomer or as a mixture of isomers (IA)

wherein
- X is halogen; nitro; $SOR_5$, $SO_2R_5$ in which $R_5$ is $C_1$–$C_6$ alkyl benzyl, phenyl, $C_2$–$C_4$ alkenyl or $C_2$–$C_4$ alkynyl; or $SO_2N(R_6)_2$ in which each $R_6$ is, independently, hydrogen, $C_1$–$C_6$ alkyl, benzyl, phenyl or $C_2$–$C_4$ alkenyl;
- Y is hydrogen; halogen; nitro; $C_1$–$C_6$ alkyl; $C_1$–$C_6$ alkoxy; $C_1$–$C_6$ alkylthio; $SOR_5$, $SO_2R_5$ in which $R_5$ is as defined above or $SO_2N(R_6)_2$ in which each $R_6$ is as defined above;
- R is hydroxy; $OR_5$ in which $R_5$ is as defined above; $N(R_6)_2$ or $N(R_6)OR_6$ in which $R_6$ is as defined above;
- $R_1$ and $R_2$ are, each independently, hydrogen, halogen, hydroxy, $C_1$–$C_6$ alkoxy, $C_1$–$C_6$ alkyl, phenyl or benzyl; or a pharmaceutically acceptable salt thereof; provided that:
  - (i) when Y and $R_2$ are both hydrogen and $R_1$ is methyl, X is not nitro;
  - (ii) when X is halogen and Y, in position 4' of the phenyl residue, is $C_1$–$C_4$ alkyl, $R_1$ and $R_2$ are not both hydrogen;
  - (iii) when X and Y, in position 4' of the phenyl residue, are both chlorine, bromine or fluorine, $R_1$ and $R_2$ are not both hydrogen;
  - (iv) when X is chlorine and Y, in position 6' of the phenyl residue, is phenyl, methyl or methoxy, $R_1$ and $R_2$ are not both hydrogen;
  - (v) when X is chlorine and Y, in position 4' of the phenyl residue, is phenyl or methoxy, $R_1$ and $R_2$ are not both hydrogen;
  - (vi) when X is bromine and Y is in position 4' of the phenyl residue, Y, $R_1$ and $R_2$ are not simultaneously hydrogen;
  - (vii) when X and Y in position 4' of the phenyl residue are both chlorine, $R_1$ is not benzyl; and
  - (viii) when, at the same time, X is halogen or phenyl, Y is hydrogen, $C_1$–$C_6$ alkyl or $C_1$–$C_6$ alkoxy, $R_2$ is hydrogen and R is hydroxy or $C_1$–$C_6$ alkoxy, then $R_1$ is other than methyl.

4. A compound as claimed in claim 3 wherein
X is halogen or nitro;
Y is hydrogen, halogen or $C_1$–$C_6$ alkoxy;
R is hydroxy or —$OR_5$ in which $R_5$ is $C_1$–$C_6$ alkyl;
$R_1$ and $R_2$ are, each independently, hydrogen, halogen, hydroxy, $C_1$–$C_6$ alkoxy, $C_1$–$C_6$ alkyl, phenyl or benzyl, or a pharmaceutically acceptable salt thereof.

5. A compound selected from:
4-(3'-fluorophenyl)-4-oxo-2-butenoic acid;
4-(3'-chlorophenyl)-4-oxo-2-butenoic acid;
4-(3'-nitrophenyl)-4-oxo-2-butenoic acid;
4-(3'-fluoro-4'-methoxyphenyl)-4-oxo-2-butenoic acid;
2-methyl-4-(3',4'-dichlorophenyl)-4-oxo-2-butenoic acid;
3-methyl-4-(3',4'-dichlorophenyl)-4-oxo-2-butenoic acid;
3-phenyl-4-(3',4'-dichlorophenyl)-4-oxo-2-butenoic acid;
3-benzyl-4-(3',4'-dichlorophenyl)-4-oxo-2-butenoic acid;
2,3-dimethyl-4-(3',4'-dichlorophenyl)-4-oxo-2-butenoic acid;
2-hydroxy-4-(3'-chlorophenyl)-4-oxo-2-butenoic acid;
2-hydroxy-4-(3'-fluorophenyl)-4-oxo-2-butenoic acid;
2-hydroxy-4-(3',4'-dichlorophenyl)-4-oxo-2-butenoic acid;
2-hydroxy-4-(3',4'-difluorophenyl)-4-oxo-2-butenoic acid;
2-hydroxy-4-(3'-chloro-4'-methoxyphenyl)-4-oxo-2-butenoic acid; either as a single isomer or as a mixture thereof or a pharmaceutically acceptable salt thereof.

6. The pharmaceutical composition of claim 3, wherein the neurodegenerative disease is Huntington's chorea, Alzheimer's disease, dementia caused by acquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections or inflammations of the brain.

7. A method of treating a patient in need of a kynurenine-3-hydroxylase inhibitor, comprising administering to said patient an effective amount of a compound as defined in claim 3, or a pharmaceutically acceptable salt thereof.

* * * * *